(12) United States Patent  
Maki et al.

(10) Patent No.: US 7,399,290 B2
(45) Date of Patent: Jul. 15, 2008

(54) MEDICAL THERAPEUTIC APPARATUS

(75) Inventors: Shin Maki, Somerset, NJ (US); Wataru Karino, Somerset, NJ (US); Hiroshi Shiono, Tokyo (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 222 days.

(21) Appl. No.: 10/868,962

(22) Filed: Jun. 17, 2004

(65) Prior Publication Data

US 2005/0020976 A1  Jan. 27, 2005

(30) Foreign Application Priority Data

Jun. 18, 2003 (JP) ............................. 2003-173958

(51) Int. Cl.
*A61M 29/00* (2006.01)
(52) U.S. Cl. .................................................. 604/96.01
(58) Field of Classification Search ............ 604/101.01, 604/102.01, 103.03, 517, 101.03, 919, 43, 604/284, 27, 96.01; 606/197, 191, 198; 601/137, 601/135, 134; 607/138
See application file for complete search history.

(56) References Cited

U.S. PATENT DOCUMENTS

| | | | |
|---|---|---|---|
| 2,477,666 A * | 8/1949 | Smallen | 601/135 |
| 2,478,786 A * | 8/1949 | Smallen | 601/137 |
| 2,642,874 A * | 6/1953 | Keeling | 604/101.03 |
| 3,977,408 A | 8/1976 | MacKew | |
| 4,636,195 A * | 1/1987 | Wolinsky | 604/509 |
| 4,660,560 A * | 4/1987 | Klein | 606/108 |
| 4,704,102 A * | 11/1987 | Guthery | 604/28 |
| 4,717,380 A | 1/1988 | Baumgartner | |
| 4,911,149 A | 3/1990 | Borodulin et al. | |
| 5,007,897 A | 4/1991 | Kalb et al. | |
| 5,419,763 A | 5/1995 | Hildebrand | |
| 5,688,239 A * | 11/1997 | Walker | 604/96.01 |
| 5,797,950 A * | 8/1998 | Takashima | 606/197 |
| 5,861,000 A * | 1/1999 | Takashima | 606/197 |
| 5,931,860 A * | 8/1999 | Reid et al. | 607/101 |
| 6,102,888 A * | 8/2000 | Walker | 604/28 |
| 6,183,437 B1 * | 2/2001 | Walker | 604/96.01 |
| 6,238,339 B1 * | 5/2001 | Fiddian-Greene et al. | 600/309 |
| 6,238,366 B1 * | 5/2001 | Savage et al. | 604/28 |
| 6,299,598 B1 * | 10/2001 | Bander | 604/101.03 |
| 6,461,327 B1 * | 10/2002 | Addis et al. | 604/101.04 |
| 6,575,932 B1 * | 6/2003 | O'Brien et al. | 604/101.01 |
| 6,682,555 B2 * | 1/2004 | Cioanta et al. | 623/1.21 |
| 6,716,252 B2 * | 4/2004 | Lazarovitz et al. | 623/23.66 |
| 6,719,717 B1 * | 4/2004 | Johnson et al. | 604/9 |
| 6,758,857 B2 * | 7/2004 | Cioanta et al. | 607/105 |
| 6,802,850 B1 * | 10/2004 | Takashima | 606/197 |
| 2002/0026209 A1 | 2/2002 | Hung | |

* cited by examiner

*Primary Examiner*—Christopher D. Koharski
(74) *Attorney, Agent, or Firm*—Buchanan Ingersoll & Rooney PC

(57) ABSTRACT

To make it possible to clean the internal part of a living body and possibly also deliver a drug into the living body, a medical therapeutic apparatus includes a liquid discharge for discharging a liquid in a living body out of the living body and a liquid delivery for introducing a liquid into the living body. The liquid is delivered to a target region of the living body, and controller controls the delivery and discharge of the liquid.

9 Claims, 14 Drawing Sheets

FIG. 4
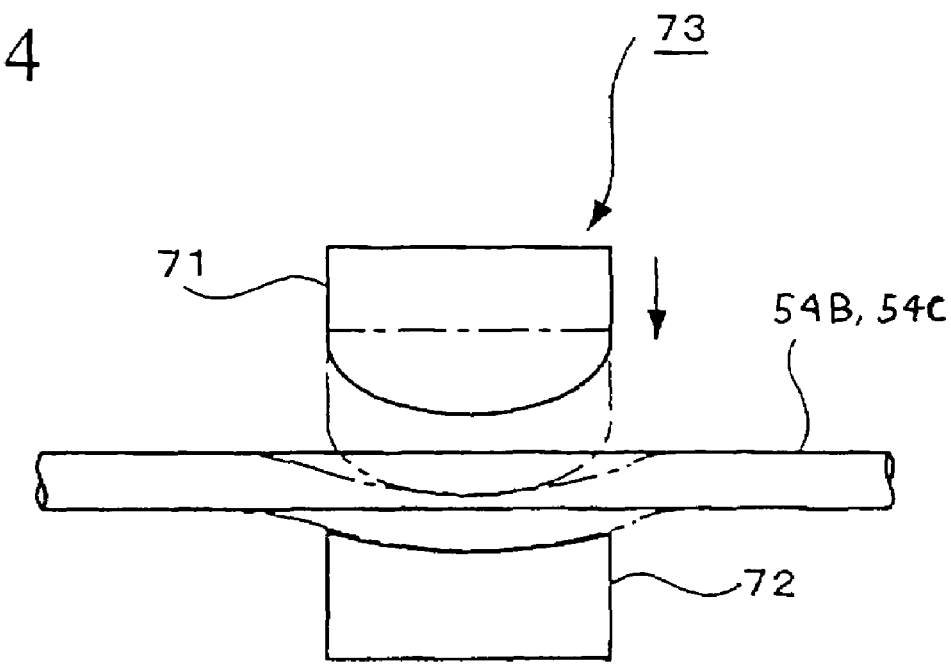
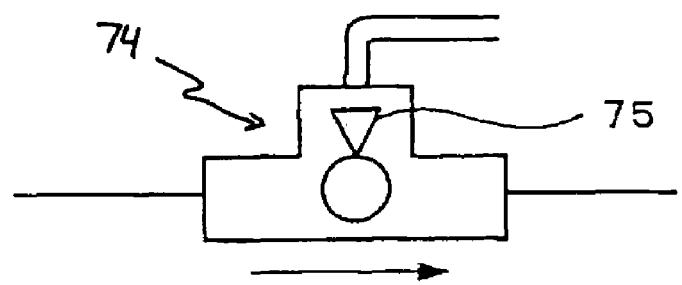
FIG. 5A
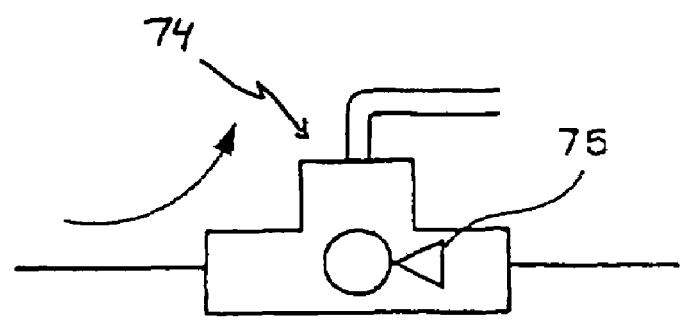
FIG. 5B

MEDICAL THERAPEUTIC APPARATUS

This application is based on and claims priority under 35 U.S.C. § 119 with respect to Japanese Application No. 2003-173958 filed on Jun. 18, 2003, the entire content of which is incorporated herein by reference.

FIELD OF THE INVENTION

The present invention generally relates to a medical therapeutic apparatus for performing therapy. More particularly, the subject matter pertains to a medical therapeutic apparatus for discharging a liquid in a living body and thereafter cleaning the living body with a liquid such as saline, drug solution, or the like or introducing such a liquid into the living body to treat, for example, prostatitis or the like. The invention also involves a medical therapeutic method.

BACKGROUND DISCUSSION

The prostatitis syndrome is generally classified into four types: 1) acute bacterial prostatitis; 2) chronic bacterial prostatitis; 3) chronic nonbacterial prostatitis; and 4) prostatic pain. Of these prostatitis symptoms, the chronic bacterial prostatitis and the chronic nonbacterial prostatitis are generally treated mainly by internally using an antimicrobial agent such as FQ (fluoroquinolone) or the like. For oral administration of a drug, the concentration of the drug as it is transferred to the prostatic fluid can be relatively important.

According to another treatment, the symptom is relieved by a prostatic massage. A bodily secretion buildup in the prostate is discharged by oozing or urging out the prostatic fluid with a hand/finger massage given by the doctor.

U.S. Pat. Nos. 3,977,408 and 5,007,897 describe apparatus for delivering a drug solution into the prostate through a balloon catheter for diagnosing prostatic diseases and making an X-ray inspection possible.

U.S. Pat. No. 5,419,763 describes an apparatus for delivering a drug solution into the prostate through a balloon catheter having second and third balloons that are positioned forward and rearward of the prostate for keeping the drug solution in the prostrate.

The prostatic massage is able to relieve the symptom, but fails to cure the disease. Also delivering a single dose of drug into the local region may not be sufficiently effective.

SUMMARY

The subject matter disclosed here provides a new therapeutic process based on cleaning, rather than simply massaging or drug administration. The therapeutic process based on cleaning is also applicable to affected areas of the living body other than the prostate. The medical therapeutic apparatus is capable of efficiently cleaning an internal part of a living body and selectively delivering a drug into the living body.

A medical therapeutic apparatus according to the present invention has liquid discharging means for discharging a liquid in a living body out of the living body, liquid delivering means for introducing a liquid into the living body, retaining means for retaining the liquid in a target position, and control means for controlling the delivery and discharge of the liquid. As used herein, liquid collectively refers to body fluids, cleaning liquids, saline, drug solutions, etc.

The medical therapeutic apparatus makes it possible for the liquid discharging means to discharge a liquid in a living body out of the living body, and for the liquid delivering means to introduce or deliver a liquid into the living body. When the liquid delivering means delivers a liquid into the living body, the liquid is delivered to the target region defined by a retaining means and so the liquid can reliably be introduced into the living body. Furthermore, by virtue of the control means which controls the delivery and discharge of the liquid, it is possible to carry out efficient cleaning in the living body or deliver a drug after the cleaning.

The delivery means and the discharge means can be configured so they share a common single passage. The retaining means used to help form the target region can be in the form of a sealing means. In this case, a pair of sealing means can be provided so that a liquid-tight target region is defined between the pair of sealing means. Alternatively, the retaining means may include a liquid-tight region extending from the sealing means toward the distal end.

It is also possible to employ a physical mechanism other than fingers or hands to contract or stimulate the living body. Additionally, the liquid delivering means may be adapted to introduce liquid under pressure into the living body. Also, the liquid may be an optional liquid selected from a plurality of liquids and introduced into the living body.

The liquid discharging means may be such that it draws in the liquid in the living body. The control means may be designed to perform repetitive cleaning by setting up an optional sequence of the delivery and discharge of the liquid. It is also possible to confirm an oozing of the liquid from the living body, with the control means then possible performing cleaning by controlling the delivery and discharge of the liquid. The liquid in the living body may be discharged, the liquid to be introduced into the living body may be selected, and then the selected liquid may be introduced under automatic control.

The apparatus may also be provided with detecting means for detecting a component contained in the discharged liquid. In this case, cleaning is finished when the amount of the component is equal to or lower than a predetermined amount as detected by the detecting means.

According to another aspect, a medical therapeutic apparatus comprises a catheter body adapted to be inserted in a living body and provided with at least one lumen through which liquid from the living body is discharged and through which cleaning liquid is delivered to the living body, at least one inflatable balloon provided on the catheter body to seal against a portion of the living body upon inflation after the catheter body is inserted into the living body, a tank connected to the at least one lumen and adapted to contain the cleaning liquid that is to be delivered to the living body, a container connected to the lumen for receiving the liquid that is discharged from the living body, and control means for controlling the discharging of the liquid from the living body to the container and the delivery of the cleaning liquid from the tank to the living body.

According to another aspect, a therapeutic medical method comprises introducing into a living body an elongated member provided with at least one lumen, sealing off in a liquid-tight manner a target region of the living body from a region outside the target region, and controlling discharge of liquid from the target region of the living body by way of the at least one lumen and delivery of cleaning liquid to the target region by way of the at least one lumen to effect therapeutic treatment of the living body.

BRIEF DESCRIPTION OF THE DRAWING FIGURES

The foregoing and additional features and characteristics of the present invention will become more apparent from the following detailed description considered with reference to the accompanying drawing figures in which like reference numerals designate like elements.

FIG. 4 is a schematic illustration of a clamp-type on-off valve that is incorporated in the liquid delivery/discharge control apparatus shown in FIG. 3.

FIGS. 5A and 5B are schematic illustrations showing the manner in which a three-way stopcock incorporated in the liquid delivery/discharge control apparatus shown in FIG. 3 operates.

DETAILED DESCRIPTION

Figure 1:
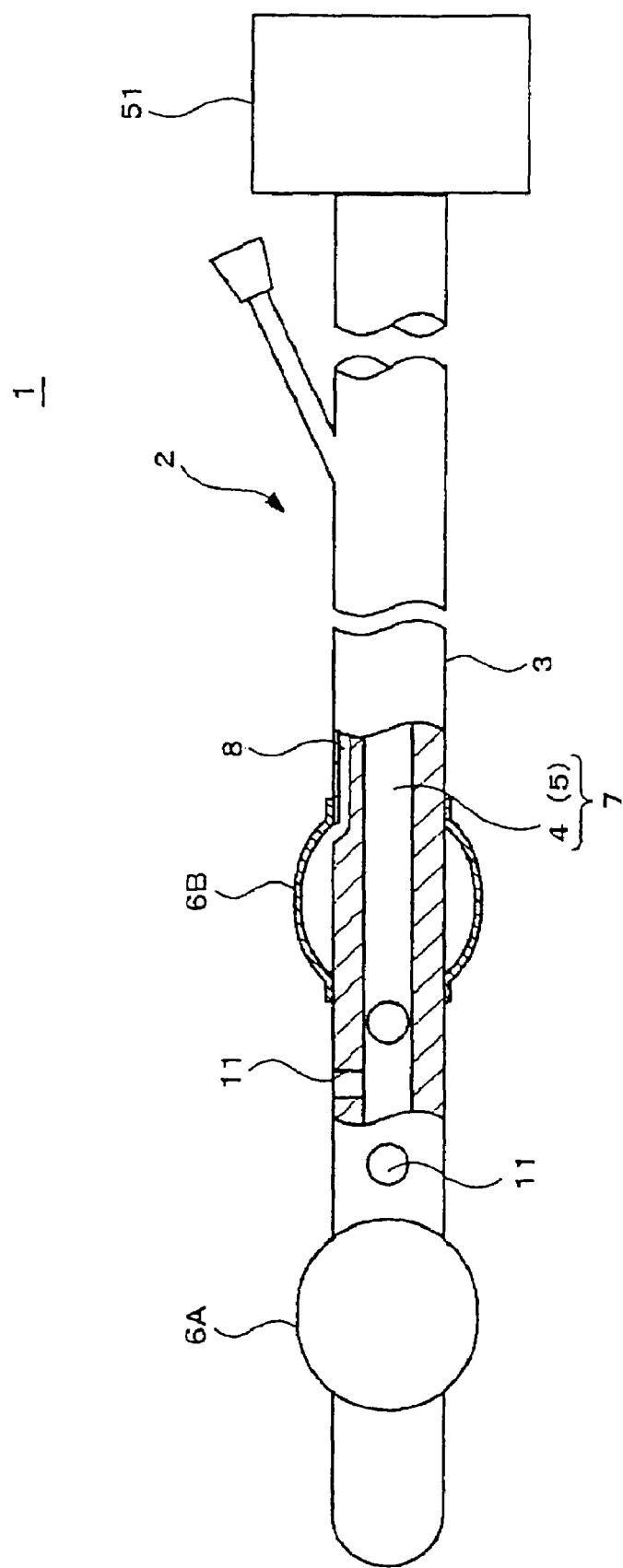
FIG. 1 is a side view schematically illustrating an embodiment of a medical therapeutic apparatus according to one possible version of the present invention.

Referring initially to FIG. 1, one embodiment of a medical therapeutic apparatus 1 includes a liquid delivery/discharge catheter 2 for discharging a liquid (including a body fluid, a liquid used for cleaning, etc.) in a living body and introducing a liquid such as a cleaning liquid, saline, a drug solution, etc., for example, into the living body. The apparatus 1 also includes a liquid delivery/discharge control apparatus 51 for controlling the discharge of a liquid in the living body from the catheter 2 and delivering a liquid such as a cleaning liquid, saline (which can be used as a cleaning liquid), a drug solution, etc., for example, into the catheter 2.

Figure 2A:
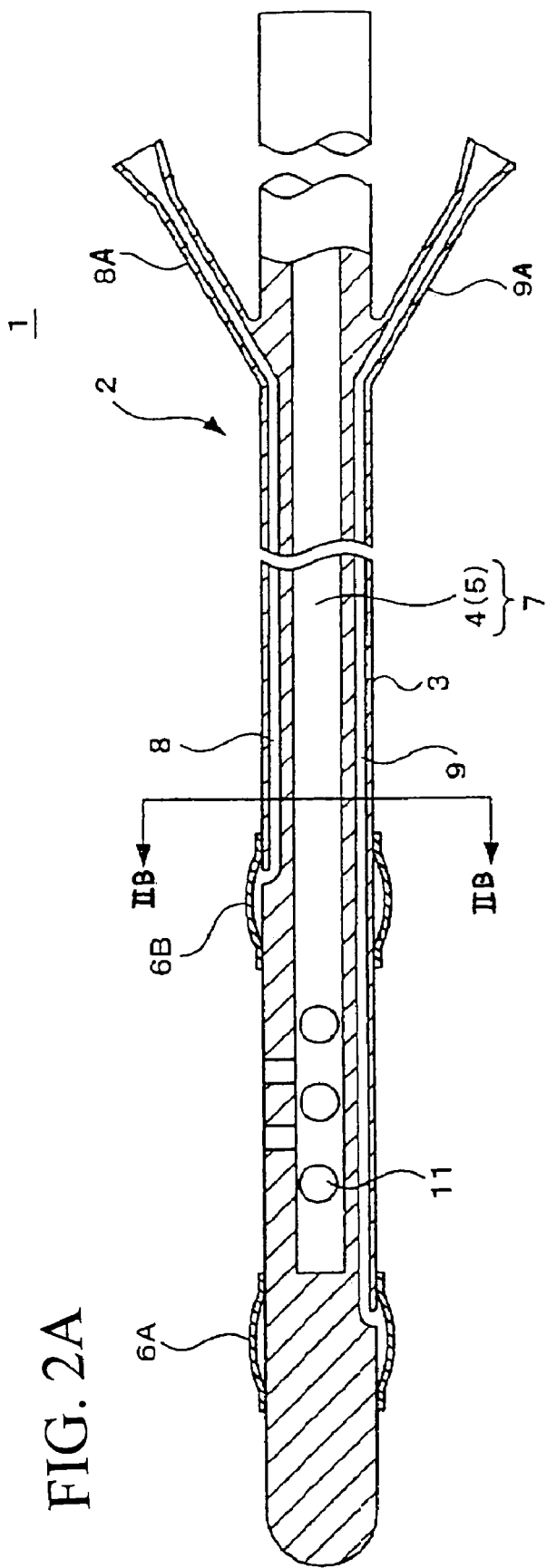
FIG. 2A is a cross-sectional view of the liquid delivery/discharge catheter shown in FIG. 1.
Figure 2B:
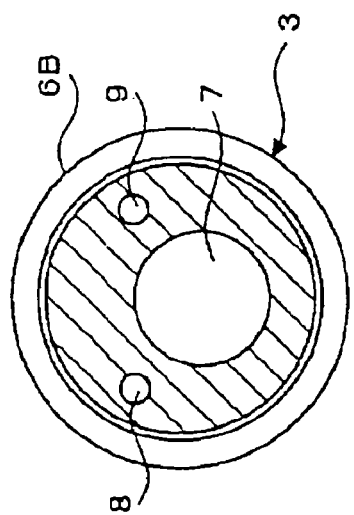
FIG. 2B is a cross-sectional view of the liquid delivery/discharge catheter taken along the section Line IIB-IIB in FIG. 2A.

As shown in FIG. 2, the liquid delivery/discharge catheter 2 is comprised of a catheter body 3 as a generally elongated insert or member. The catheter body 3 is provided with liquid discharging means 4 for discharging out of the living body a liquid (e.g., a body fluid, a cleaning liquid after it is used in cleaning, etc.) in a target region in the living body, a liquid delivering means 5 for introducing a liquid (for example saline for use in cleaning or dosing, a drug solution, etc.) into a target region in the living body, and a pair of sealing devices 6A, 6B for sealing a gap between the catheter body 3 and the living body at both end portions (i.e., the distal and rear end portions) of the catheter body 3 inserted in the living body. In this example, a single lumen 7 defined in the catheter body 3 serves as a liquid passage shared by or constituting both the liquid discharging means 4 and the liquid delivering means 5. The sealing devices 6A, 6B include expandable balloons disposed respectively on the distal and rear end portions of the catheter body 3 that is inserted in the living body. The balloons 6A, 6B define a fluid-tight living body luminal region between which serves as a retaining means for retaining a liquid.

The elongated catheter body 3 has the lumen 7 for delivering and discharging liquid, with the lumen 7 serving as a passage for delivering and discharging a liquid parallel to or along the axis of the catheter body 3. The catheter body 3 also has lumens 8, 9 for introducing air into the respective balloons 6A, 6B on the distal and rear ends of the portion of the catheter body which is inserted in the living body. The lumens 8, 9 have respective ends communicating with respective air inlets 8A, 9A that extend so as to branch from the catheter body 3. The catheter body 3 has a side wall extending along the lumen 7 provided with a plurality of through holes 11.

The catheter body 3 may be made of a hard material such as metal, e.g., SUS or the like, or a soft material such as polytetrafluoroethylene (PTFE), SEBS (thermoplastic elastomer), polyurethane, polyethylene terephthalate (PET), polyvinyl chloride, silicone rubber, latex, or the like.

Figure 3:
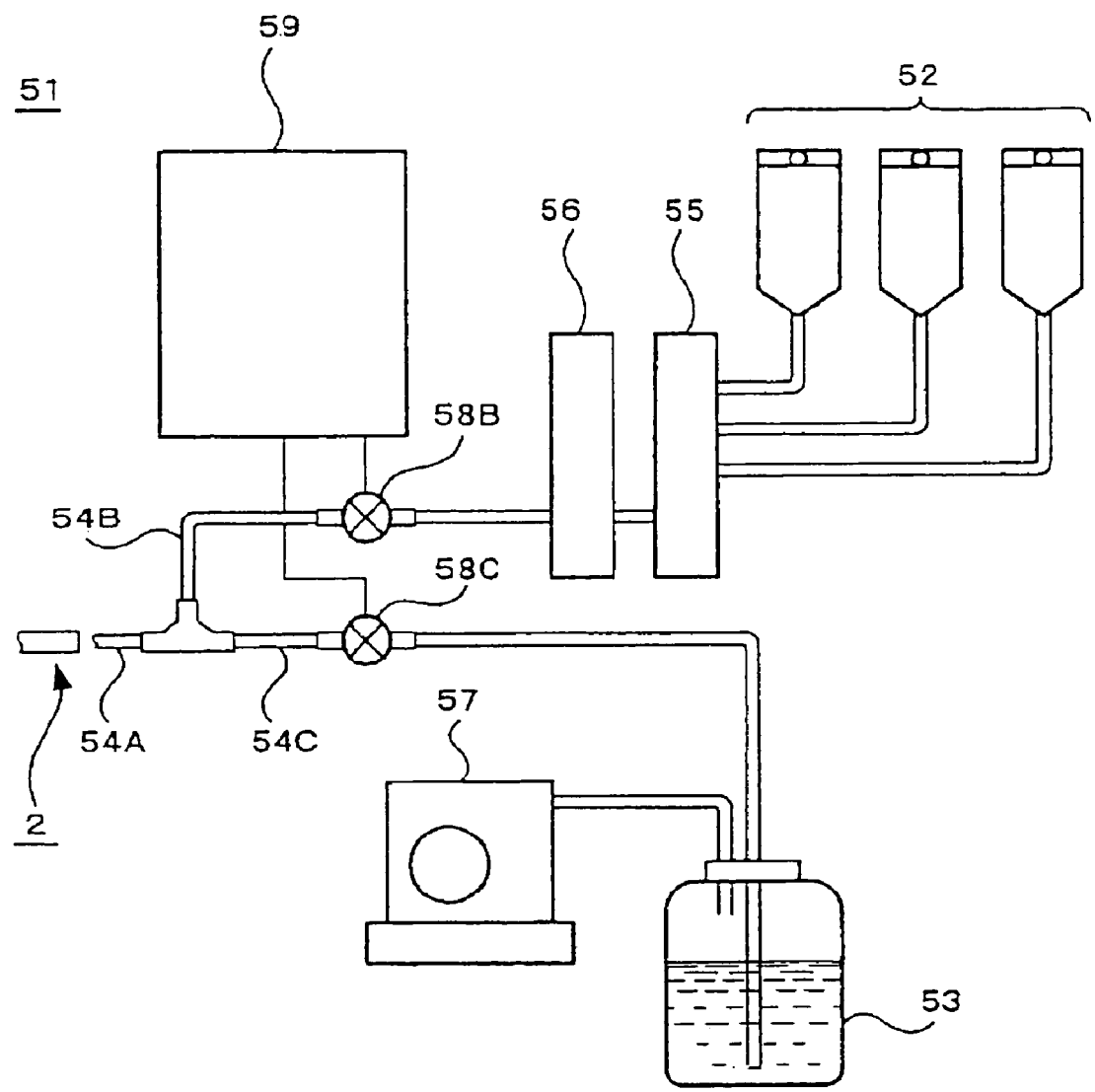
FIG. 3 is a schematic illustration of an embodiment of a liquid delivery/discharge control apparatus.

FIG. 3 shows an example of the liquid delivery/discharge control apparatus which is connected to the liquid delivery/discharge catheter 2 of the medical therapeutic apparatus 1. The liquid delivery/discharge control apparatus is disposed outside the living body and is adapted to retrieve liquid discharged from the living body and selectively deliver cleaning liquid and a plurality of drug solutions. The liquid delivery/discharge control apparatus 51 is comprised of a tank group 52 including drug solution tanks containing the respective drug solutions and a cleaning liquid tank containing a cleaning liquid such as saline or the like. The apparatus also includes a trap container 53 for retrieving, under suction, a liquid (e.g., a body fluid colonized by bacteria or the like, a liquid contaminated after it is used in cleaning). The tank group 52 is disposed on the side of a liquid-delivery second pipe 54B while the trap container 53 is disposed on the side of a liquid-retrieval third pipe 54C. The liquid-delivery second pipe 54B and the liquid-retrieval third pipe 54C branch from a first pipe 54A that is connected to the lumen 7 of the liquid delivery/discharge catheter 2.

The first pipe 54A, the second pipe 54B and the third pipe 54C are connected to each other by a switching valve which may be in the form of a three-way stopcock 74 as shown in FIGS. 5A and 5B. FIG. 5A shows a state of the stopcock 74 in which the second pipe 54B is closed at an arrow (plug) 75, while providing communication between the passages of the first pipe 54A and the third pipe 54C. FIG. 5B shows a state of the stopcock in which the third pipe 54C is closed at the arrow (plug) 75, while providing communication between the passages of the first pipe 54A and the second pipe 54B.

The tanks of the tank group 52 are connected by pipes to a liquid selector 55 for selecting a cleaning liquid and drug solutions. The liquid selector 55 is connected to a liquid supply 56 which delivers a selected liquid under a predetermined pressure to the catheter body 3. The third pipe 54C is inserted in the trap container 53, and a suction hose of a vacuum pump 57 is also inserted in the trap container 53 out of contact with the liquid retrieved in the trap container 53.

An on-off valve controller 59 selectively opens and closes on-off valves, e.g., solenoid-operated valves 58B, 58C disposed respectively in the second and third pipes 54B, 54C. The on-off valve controller 59 also controls the three-way stopcock 74. As shown in FIG. 4, each of the on-off valves 58B, 58C may include, rather than a solenoid-operated valve, a so-called clamp-type on-off valve 73 having a presser 71 and a receiver 72 which are disposed on opposite sides of the pipe 54B, 54C that is flexible, for grippingly pressing and releasing the pipe 54B, 54C to close and open the pipe 54B, 54C.

Separate apparatus are provided which are connected to the lumens 8, 9 coupled to the balloons for delivering and discharging air to control the expansion and contraction of the balloons 6A, 6B. The balloons 6A, 6B may be expanded and contracted by a desired gas or liquid, rather than air.

If a liquid is delivered of its own accord rather than under a positive pressure, the liquid supply 56 which has a pump for applying a positive pressure may be dispensed (i.e., may be unnecessary). If a liquid is discharged of its own accord rather than under a negative pressure, then the vacuum pump 57 may also be dispensed.

The operation of the apparatus 1 is as follows. When a liquid discharged out of a living body is to be retrieved outside of the living body, the on-off valve 58B of the second pipe 54B is closed and the on-off valve 58C of the third pipe 54C is opened by a command from the on-off valve controller 59. At the same time, the plug of the three-way stopcock 74 is turned to bring the first pipe 54A and the third pipe 54C into communication with each other by a command from the on-off valve controller 59. The vacuum pump 57 is actuated to retrieve a liquid which oozes or is discharged from the living body into the catheter body 3, through the third pipe 54C into the trap container 53. When a liquid is to be delivered into the living body, the second pipe 54B is opened and the third pipe 54C is closed by a command from the on-off valve controller 59. At the same time, the plug of the three-way stopcock 74 is turned to bring the first pipe 54A and the second pipe 54B into communication with each other by a command from the on-off valve controller 59. The liquid selector 55 selects the liquid in a tank of the tank group 52. The selected liquid is supplied to the lumen 7 of the catheter body 3 via the liquid supply 56 and introduced into the living body.

It is to be noted that in the above-described embodiment, the on-off valves 58B and 58C may be omitted as long as the apparatus 1 has the three-way stopcock 74 which is the valve controlling the change of liquid passages (pipe 54A, 54B). The three-way stopcock 74 may be manually operated.

An example of one possible usage of the medical therapeutic apparatus 1 will be described below. In this example, the medical therapeutic apparatus 1 is applied to the treatment of prostatitis, particularly, chronic bacterial prostatitis and chronic nonbacterial prostatitis.

Figure 6:
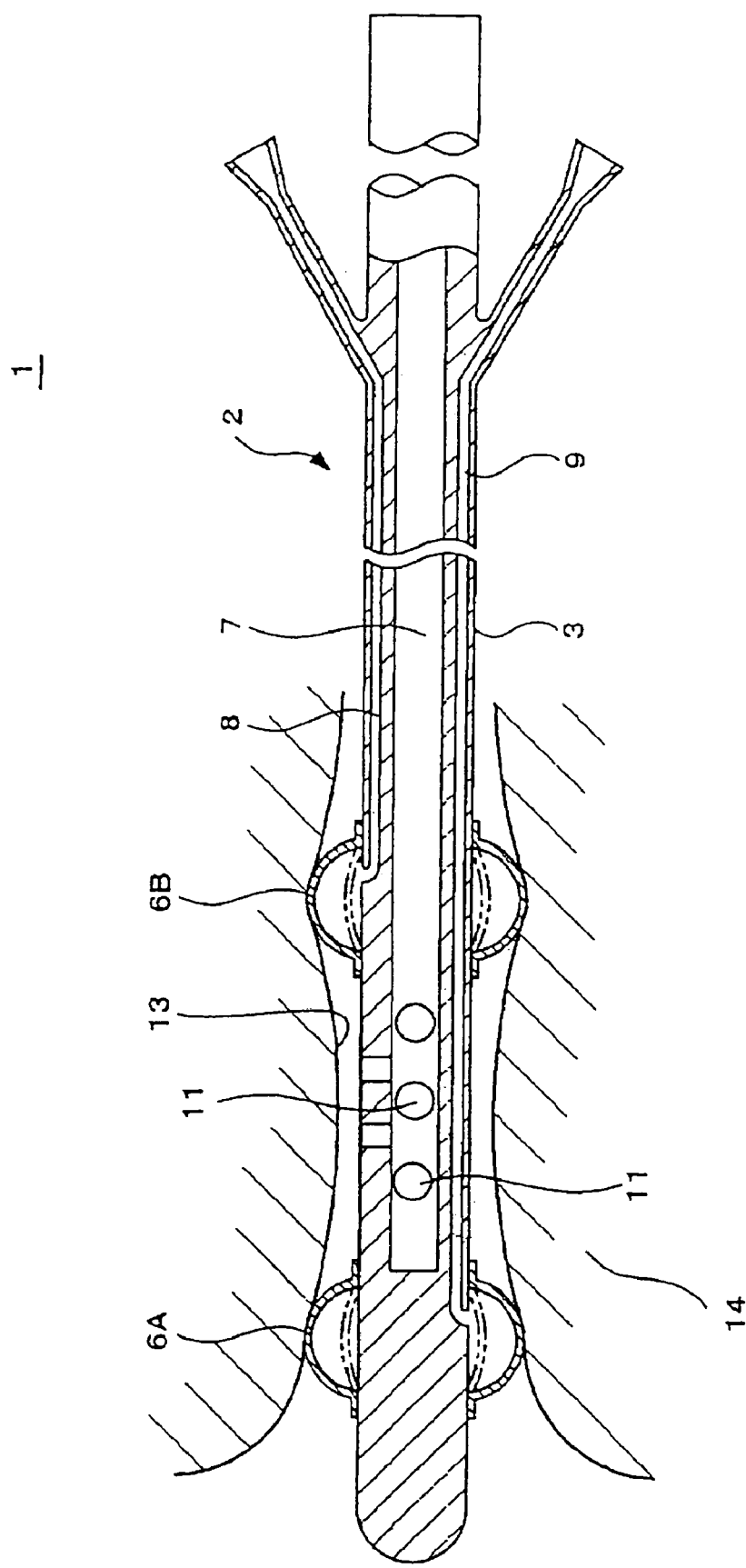
FIG. 6 is a cross-sectional view of the liquid delivery/discharge catheter of FIGS. 1 and 2 showing a manner of using the catheter together with the medical therapeutic apparatus.

As shown in FIG. 6, the catheter body 3 on the distal end portion of the liquid delivery/discharge catheter 2 of the medical therapeutic apparatus 1 is inserted into a body cavity in a living body, (i.e., a urinary tract 13) and is stopped at a living body tissue to be treated, i.e., at a position corresponding to a prostate gland 14. Then, air is introduced through the air inlets to expand the balloons 6A, 6B into intimate contact with the urinary tract wall, thus sealing the urinary tract region between the balloons 6A, 6B in a fluid-tight fashion. It is preferable to bring the balloons 6A, 6B into intimate contact with the living body at the bladder neck region and the external urinary sphincter.

Figure 7A:
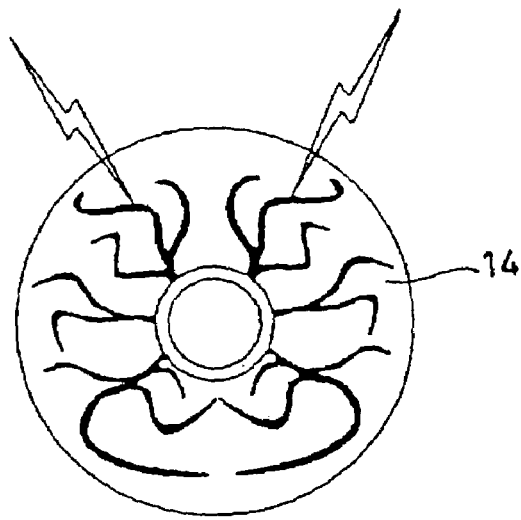
FIGS. 7A to 7C are views illustrating the manner in which a liquid in the prostate gland is replaced.
Figure 7B:
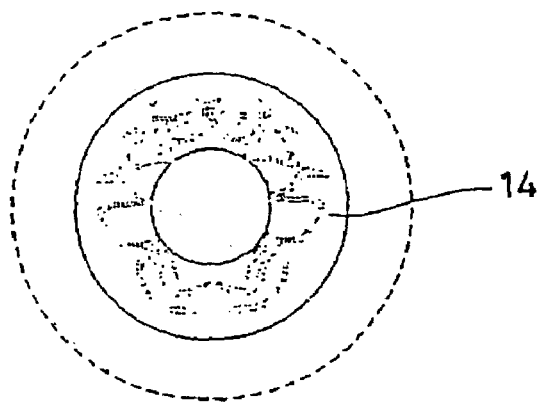

Then, a stimulus (e.g., pressing, massaging, or the like) is applied to the prostate gland 14 to contract the prostate gland 14, causing the bodily secretion (prostatic fluid or pus) in the prostate gland 14 to ooze out or be discharged. That is, the bodily secretion is positively forced out. FIG. 7A shows a state immediately before the prostatic fluid is forced out. FIG. 7B shows a contracted state of the prostate gland 14 at the time the prostate gland 14 is contracted to force out the prostatic fluid which is suffering a bacterial infection. The prostate gland 14 may be stimulated by physical means, other than hands and fingers, which the doctor applies from within the rectum to massage or press the prostate gland. The physical means is a device which may be vibration, pressing, or friction. The bodily secretion that has oozed out or been forced out is discharged from the through holes 11 of the catheter body 3 inserted in the urinary tract 13 through the lumen 7 out of the living body. At this time, the bodily secretion can be discharged via the first pipe 54A connected to the lumen 7 and the third pipe 54c into the trap container 53 under suction forces which are not strong enough to strain the prostate gland 14. Massaging causes a muscular contraction to contract the prostate gland 14 whereas pressing directly contracts the prostate gland 14 itself.

Figure 7C:
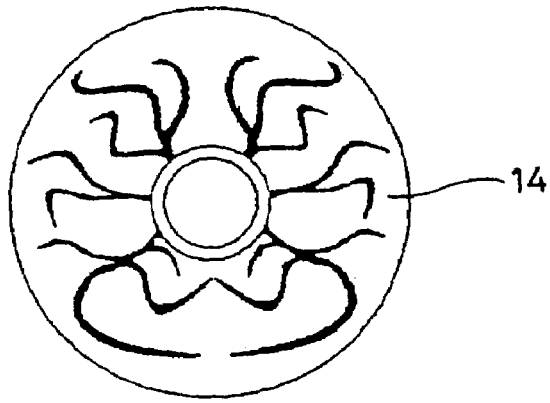

After the bodily secretion is discharged from the prostate gland 14, a cleaning liquid such as, for example, saline or the like is delivered via the second pipe 54B and the first pipe 54A into the lumen 7, cleaning the prostate gland 14. At this time, the cleaning liquid is delivered into the prostate gland 14 such that the delivered liquid is temporarily retained in the region in the urinary tract which corresponds to the prostate gland 14 that is sealed by the balloons 6A, 6B. It is preferable to deliver the cleaning liquid under a required positive pressure. When the pressing or the massaging of the prostate gland 14 is stopped, a cleaning liquid is introduced into the prostate gland 14 under suction forces that are produced upon relaxation of the contracted prostate gland 14. FIG. 7C shows a state in which the stimulus is canceled and the prostate gland 14 is expanded. After the cleaning liquid is introduced, the prostate gland 14 is contracted by being pressed or massaged, discharging the cleaning liquid in the prostate gland 14 through the lumen 7. This process is repeated several times to clean the prostate gland 14. The process is automatically repeated by opening and closing the flow passages provided by the first pipe 54A, the second pipe 54B, and the third pipe 54C.

After the cleaning process is ended, the liquid delivery/discharge control apparatus 51 switches from the cleaning liquid to a drug solution. The liquid delivery/discharge control apparatus 51 introduces the drug solution through the lumen 7 into the prostate gland 14 in the same manner as described above, whereupon the treatment is put to an end or stops. In some cases, the treatment may be ended only by cleaning the prostate gland 14 with saline. Alternatively, the treatment may be ended only by cleaning the prostate gland 14 with a liquid which is a mixture of saline and a drug solution. After the cleaning and the delivery of the drug solution are finished, the balloons 6A, 6B are contracted, and the catheter body 3 is removed from the urinary tract 13, whereupon the whole process is ended. As mentioned above, the balloons 6A, 6B may be expanded and contracted by a desired gas or liquid, rather than air.

Examples of the drug solution that are used in treating prostatitis with the medical therapeutic apparatus according to the embodiment are shown in Table 1.

TABLE 1

| antimicrobial drugs | Penicillins |
| --- | --- |
| | Ampicillins |
| | wide-range spectrum (anti-*Pseudomonas aeruginosa* activity) penicillins |
| aminoglycoside | Gentamicin |
| tetracycline-based antimicrobial drug | tetracycline |
| others | Chloramphenicol |
| | Nitrofrantoin |
| quinolone-based (bactericidal) | fluoroquinolone |
| sulfonamids | Sulfasoxazole |
| | Sulfamethoxazole |
| trimethoprim-sulfamethoxazole (TMP-SMX) | |

In the above-described example, the liquid is discharged by being positively drawn. However, rather than being drawn, the liquid may be discharged of its own accord under its head or a natural contraction at the time the prostate gland returns to its original state from the expanded state in which the liquid is introduced into the prostate gland. The liquid may also be delivered, not under a positive pressure, but of its own accord under its head or a natural expansion at the time the prostate gland returns to its original state from the contracted state in which the liquid is discharged. The repetitive process of discharging and delivering the liquid of its own accord may be automatically carried out by opening and closing the flow passages provided by the pipes 54A, 54B, 54C, i.e., opening and closing the on-off valves 58 and the three-way stopcock 74 which may be solenoid-operated valves and clamp-type valves. The above-described process of discharging and delivering the liquid of its own may be applied to the cleaning and dosing of living body regions other than the prostate gland.

Figure 11:
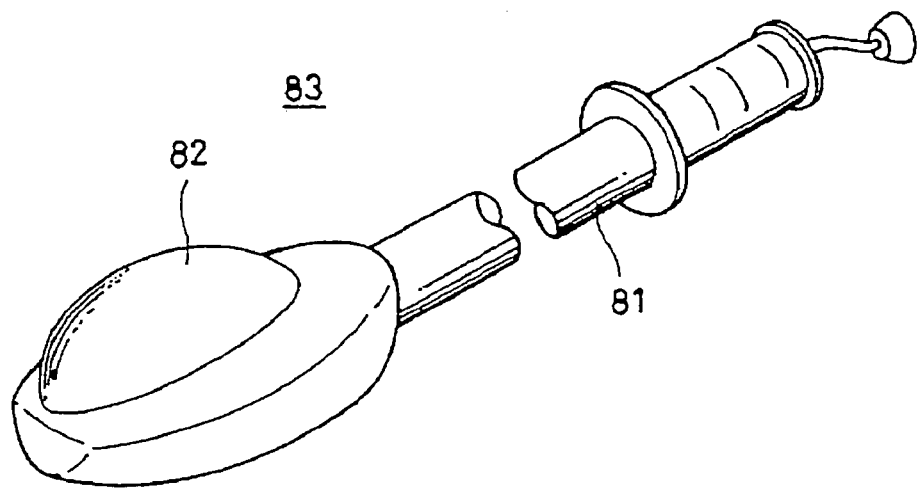
FIG. 11 is a perspective view of a portion of an example of a pressing device incorporated in or used together with the medical therapeutic apparatus.
Figure 12:
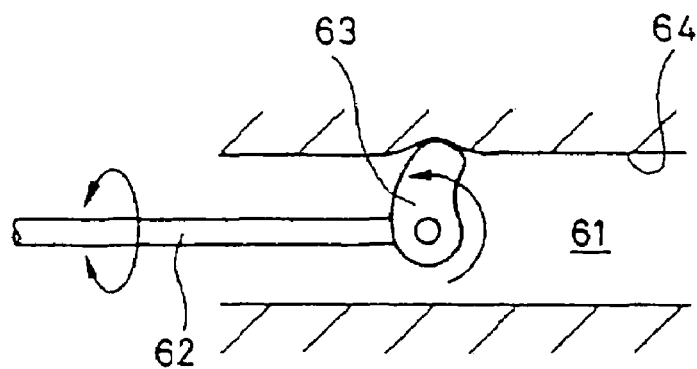
FIG. 12 is a side view illustrating an example of a massaging device incorporated in the medical therapeutic apparatus.

For stimulating (e.g., pressing) the prostate gland under water or air pressure, there may be used, as shown in FIG. 11, a stimulating device 83 having a balloon 82 made of a relatively soft rubber membrane which is disposed on the distal end of a catheter 81 to be inserted into the rectum 64 (shown in FIG. 12). The stimulating device 83 is inserted into the rectum 64, and the water or air pressure introduced into the balloon 82 is controlled to increase or reduce the pressure applied to the inner wall of the rectum 64 by the balloon 82, thus pressing the prostate gland 14.

Figure 13:
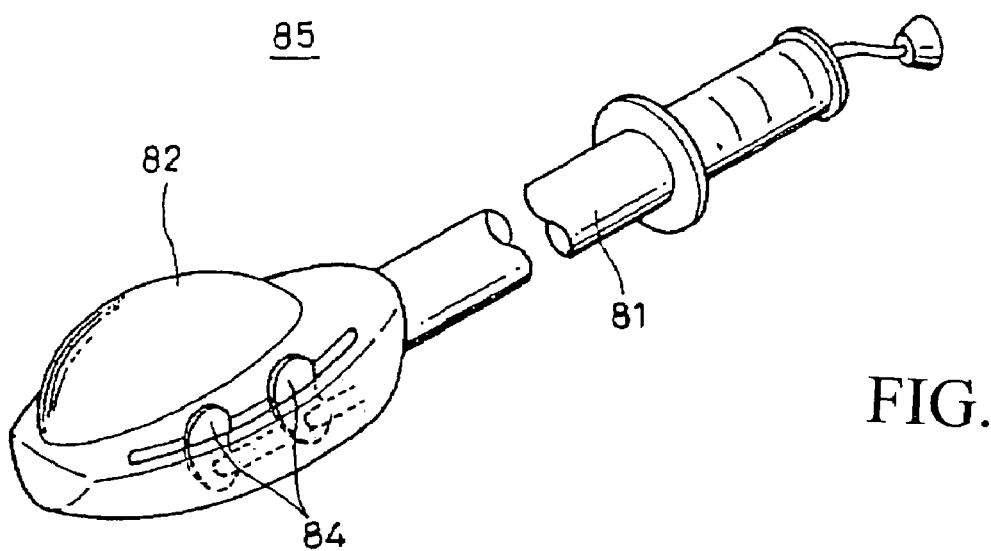
FIG. 13 is a perspective view of another example of a pressing device incorporated in the medical therapeutic apparatus.

Alternatively, as shown in FIG. 13, it is possible to use a stimulating device 85 having a balloon 82 made of a relatively soft rubber membrane which is disposed on the distal end of a catheter 81 to be inserted into the rectum, and massaging means 84 disposed near the balloon 82. The stimulating device 85 is inserted into the rectum 64, and the water or air pressure introduced into the balloon 82 is controlled to increase or reduce the pressure that is applied to the inner wall of the rectum 64 by the balloon 82, thus pressing the prostate gland 14, or the massaging means 84 is actuated to massage the prostate bland 14.

FIG. 12 shows an example of a mechanism for stimulating the prostate gland. In this example, a massaging device 61 includes a rotor 63 (e.g., nail-shaped or kidney shaped) mounted on the distal end of a rotational shaft 62 which is rotated by a motor, with the rotor 63 being rotatable in a plane perpendicular to the rotational shaft 62.

The massaging device 61 is used as follows. The rotor 63 is inserted into the rectum 64, and the motor is energized to rotate the rotor 63 in contact with the inner wall of the rectum 64 to thereby stimulate the prostate gland 14 by way of friction or vibration.

The medical therapeutic apparatus 1 according to the present embodiment is capable of efficiently treating a living body region by repeatedly and efficiently cleaning or directly selectively dosing the living body region. The medical therapeutic apparatus 1 is suitable for treating chronic bacterial prostatitis and chronic nonbacterial prostatitis.

If the medical therapeutic apparatus has physical means, other than hands and fingers, for contracting the prostate gland 14, the efficiency of massaging and pressing operation can be increased, and a liquid can efficiently be discharged. Also, by introducing a liquid into the prostate gland 14 in exchange for the body fluid, the prostate gland 14 can be cleaned, and the prostate gland 14 can be directly dosed.

By replacing a liquid (the body fluid, the cleaning liquid, or the drug solution) in the prostate gland 14 under automatic control, the prostate gland 14 can be efficiently cleaned for increased therapeutic efficiency. Also, by selecting an optional liquid from a plurality of liquids, e.g., the cleaning liquid and the drug solution, and introducing the selected liquid into the prostate gland 14, the prostate gland 14 can be efficiently cleaned, and the prostate gland 14 can be dosed. Additionally, performing repetitive cleaning by setting up an optional sequence of the delivery and discharge of the liquid with the control apparatus 51 makes it possible to more efficiently clean the prostate gland 14. Further, by confirming oozing or discharge of the liquid from the prostate gland 14 and performing cleaning by controlling the delivery and discharge of the liquid with the control apparatus 51, the affected area can more reliably be cleaned.

Figure 8:
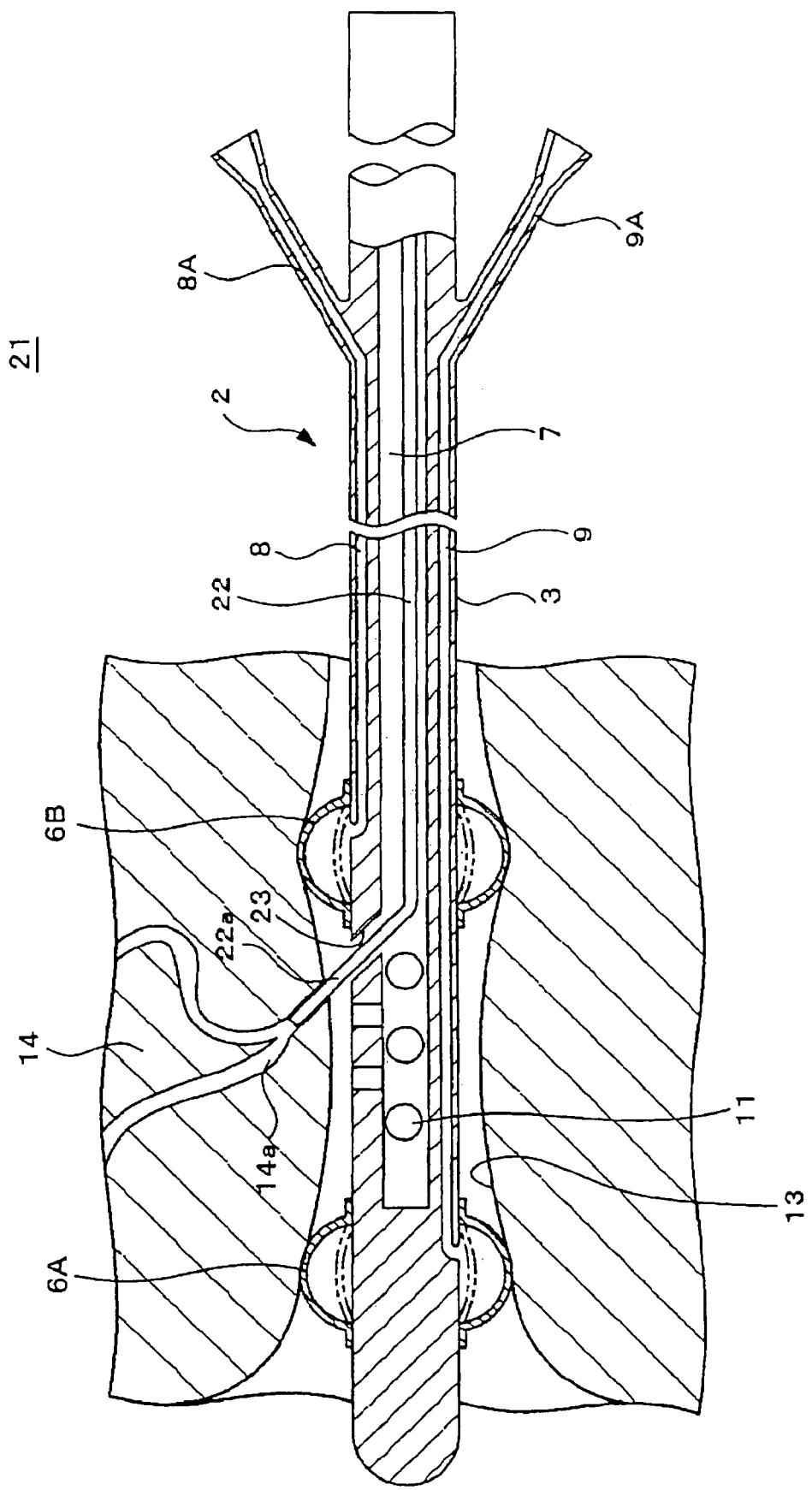
FIG. 8 is a cross-sectional view of another embodiment of the liquid delivery/discharge catheter.

FIG. 8 shows a medical therapeutic apparatus according to another embodiment. Here, the medical therapeutic apparatus 21 comprises the catheter body 3 of the medical therapeutic apparatus 1 described above that is adapted to be inserted into the living body, and a delivery/discharge tube body 22 disposed in the catheter body 3 parallel to the axis of the catheter body 3 as a passage for a liquid that is delivered and discharged. A plurality of slender tubes 22a branch from the distal end portion of the tube 22 and have respective distal ends movable into and out of the catheter body 3 via a through hole 23 defined in the catheter body 3. Other structural details are the same as those shown in FIG. 2 and described above. Parts in the embodiment shown in FIG. 8 which correspond to those shown in FIG. 2 are denoted by identical reference characters, and a description of such features will not be repeated here.

With the medical therapeutic apparatus 21 shown in FIG. 8, either the lumen 7 or the tube body 22 may be selected for delivering and discharging liquids for treatment. When the lumen 7 is selected, the medical therapeutic apparatus 21 is used in the same manner as described above. When the tube body 22 is selected, the slender tubes 22a of the tube body 22 are inserted from the through hole 23 into the living body. For example, for treating prostatitis, the slender tubes 22a are inserted into a gland cavity 14a of the prostate gland 14. Then, the prostate gland 14 is repeatedly stimulated and relieved in the same manner as described above, and the liquid in the gland cavity 14a of the prostate gland 14 is replaced and the prostate gland 14 is cleaned and dosed through the tube body 22. The medical therapeutic apparatus 21 is thus able to efficiently perform a therapeutic process in the same manner as with the above medical therapeutic apparatus 1.

Figure 9A:
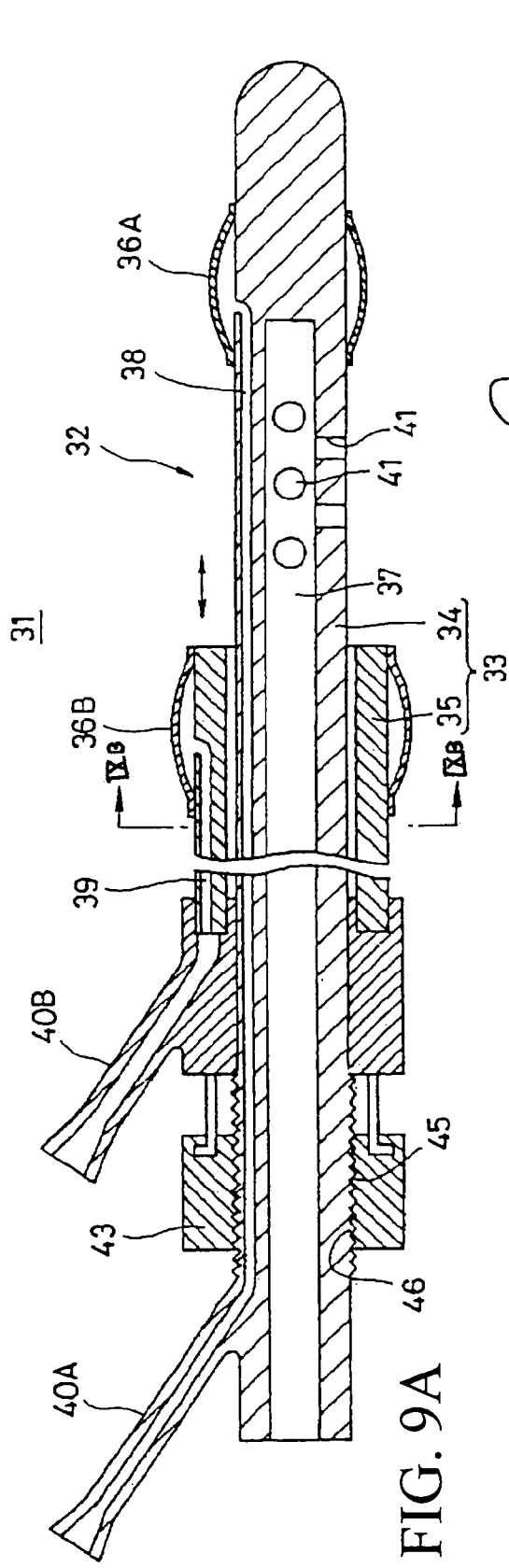
FIG. 9A is a cross-sectional view of another embodiment of the liquid delivery/discharge catheter.
Figure 9C:
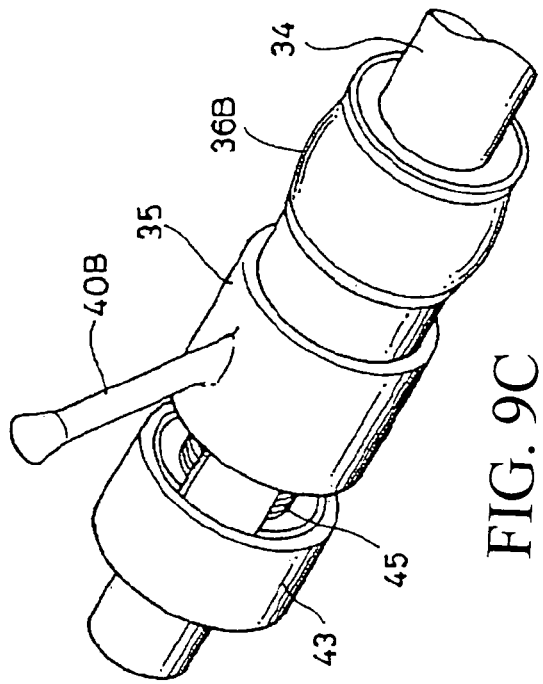
FIG. 9C is a perspective view of a portion of the liquid delivery/discharge catheter shown in FIG. 9A.
Figure 9B:
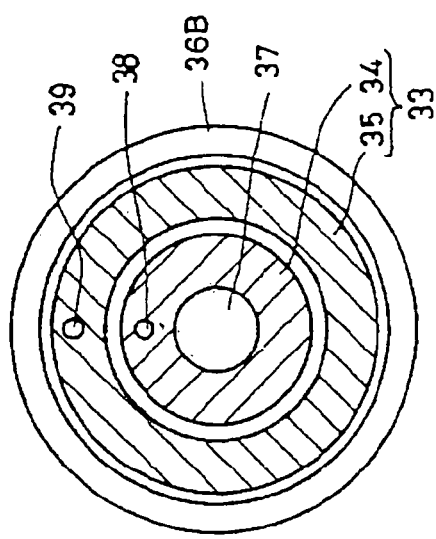
FIG. 9B is a cross-sectional view of the liquid delivery/discharge catheter taken along the section line IXB-IXB of FIG. 9A.

FIG. 9 shows a medical therapeutic apparatus according to still another embodiment. In this version, the medical therapeutic apparatus 31 has a liquid delivery/discharge catheter 32 for discharging a liquid in a living body and introducing a liquid such as saline, a drug solution, or the like into the living body. The apparatus 31 also comprises a liquid delivery/discharge control apparatus 51 like that described above.

The liquid delivery/discharge catheter 32 is comprised of a catheter body 33 formed as an elongated insert or member. The catheter body 33 includes an inner catheter member 34 and a sheath 35 movably disposed outside of the inner sheath 34. A pair of balloons 36A, 36B serving as sealing devices are disposed between the distal end of the inner catheter member 34 and the distal end of the sheath 35.

The inner catheter member 34 has a liquid delivery/discharge lumen 37 for delivering and discharging a liquid, which serves as a passage for delivering and discharging a liquid parallel to or along the axis of the catheter body 33, and a lumen 38 for introducing a liquid or a gas to expand the balloon 36A. The lumen 38 has an end communicating with an inlet 40A extending so as to branch from the inner catheter member 34. A plurality of through holes 41 are defined in the side wall of the liquid delivery/discharge lumen 37. The sheath 35 has a lumen 39 for introducing a liquid or a gas to expand the balloon 36B. The lumen 39 has an end communicating with an inlet 40B extending so as to branch from the sheath 35.

The inner catheter member 34 has an externally threaded surface 45 on its end which is positioned out of the living body. A position setting member 43 has an internally threaded surface 46 held in threaded engagement with the externally threaded surface 45 for setting a fixed position for the balloons 36A, 36B. The sheath 35 is mounted on the position setting member 43 for rotation about the inner catheter member 34 and movement in unison with the position setting member 43 in the axial direction of the inner catheter member 34.

One example of a usage of the medical therapeutic apparatus 31 shown in FIG. 9A will be described below. In this example, the medical therapeutic apparatus 1 is applied to the treatment of prostatitis, particularly, chronic bacterial prostatitis and chronic nonbacterial prostatitis, as with the previous embodiment.

Figure 10:
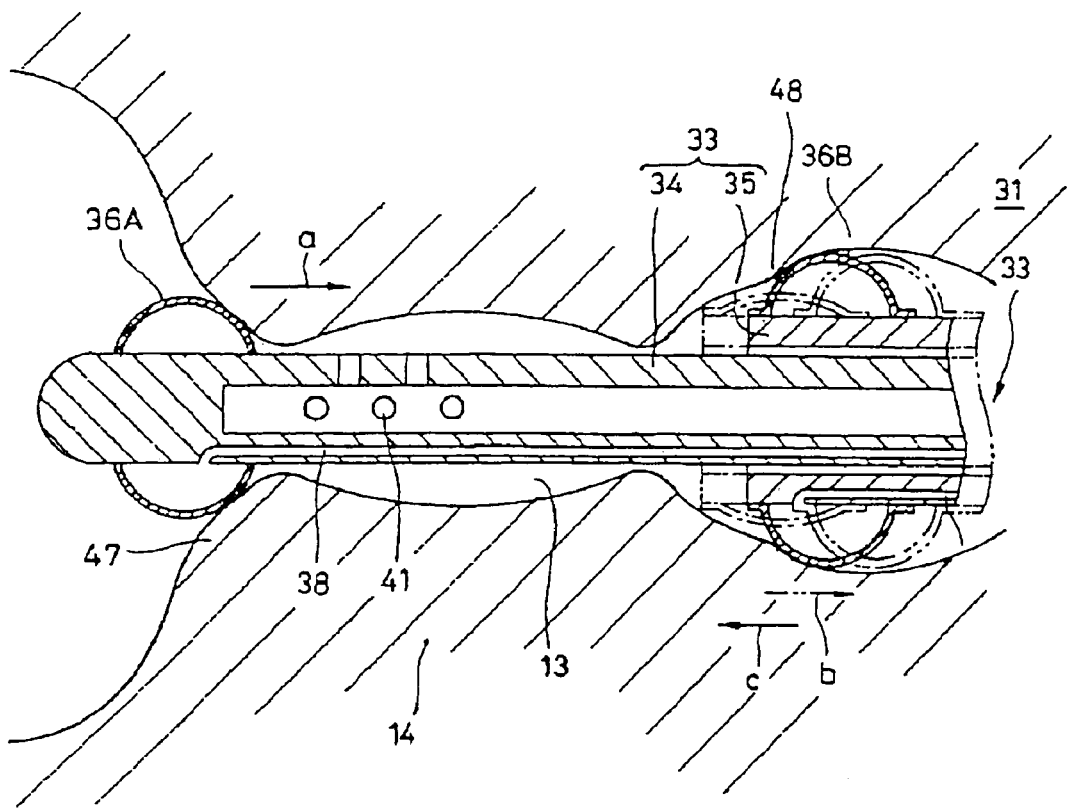
FIG. 10 is a cross-sectional view of the liquid delivery/discharge catheter of FIGS. 9A-9B showing a manner of using the catheter together with the medical therapeutic apparatus.

Referring to FIG. 10, the distal end portion of the catheter body 33 of the medical therapeutic apparatus 31 is inserted into a body cavity in a living body, i.e., the urinary tract 13. The balloon 36A on the distal end of the inner catheter member 34 is inserted up to the position of a bladder neck region 47. A liquid or a gas is delivered into the lumen 38 to expand the balloon 36A. Then, the catheter body 33 itself is retracted (pulled) in the direction indicated by the arrow a to bring the balloon 36A into engagement (intimate contact) with the bladder neck region 47 and secure the position of the balloon 36A on the distal end of the inner catheter member 34.

Then, the position setting member 43 is turned to retract the sheath 35 in the direction indicated by the arrow b (which is the same direction as the direction indicated by the arrow a) to positionally align the balloon 36B of the sheath 34 with an external urinary sphincter 48. A liquid or a gas is delivered into the lumen 39 to expand the balloon 36B. Then, the position setting member 43 is turned back to move the sheath 35 in the direction indicated by the arrow c (which is the opposite direction to the direction indicated by the arrow b) to bring the balloon 36B into intimate contact with the side wall of the unitary tract in engagement with the external urinary sphincter 48, thus securing the position of the balloon 36B. At this time, as the position setting member 43 is operated to move the balloon 36B in the direction indicated by the arrow c, the balloons 36A, 36B are pressed respectively against the bladder neck region 47 and the external urinary sphincter 48, sealing a unitary tract region between the balloons 36A, 36B in a light-tight manner. At the same time, the balloons 36A, 36B can retain the introduced liquid in a target body region, i.e., a unitary tract region corresponding to the prostate gland 14, thus providing a retaining mechanism for liquid introduced into the unitary tract region corresponding to the prostate gland 14 between the balloons 36A, 36B.

With the medical therapeutic apparatus 31 held in the above state, the prostate gland 14 is repeatedly stimulated and relieved in the same manner as described above, and the liquid in the prostate gland 14 is replaced and the prostate gland 14 is cleaned and dosed through the liquid delivery/discharge lumen 37.

The medical therapeutic apparatus 31 can perform an efficient therapeutic process as with the medical therapeutic apparatus 1 described above. In particular, the two balloons 36A, 36B of the medical therapeutic apparatus 31 engage the bladder neck region and the external urinary sphincter, respectively, and the balloons 36A, 36B are pressed against the external urinary sphincter in mutually opposite directions. Therefore, the urinary tract region between the balloons 36A, 36B is completely sealed in a light-tight fashion, providing a retaining mechanism for liquid when the liquid is introduced into the prostate gland 14. Therefore, even when the liquid is introduced into the prostate gland 14 under positive pressure, the positive pressure is not released, and the liquid can reliably be introduced into the prostate gland 14.

Figure 14:
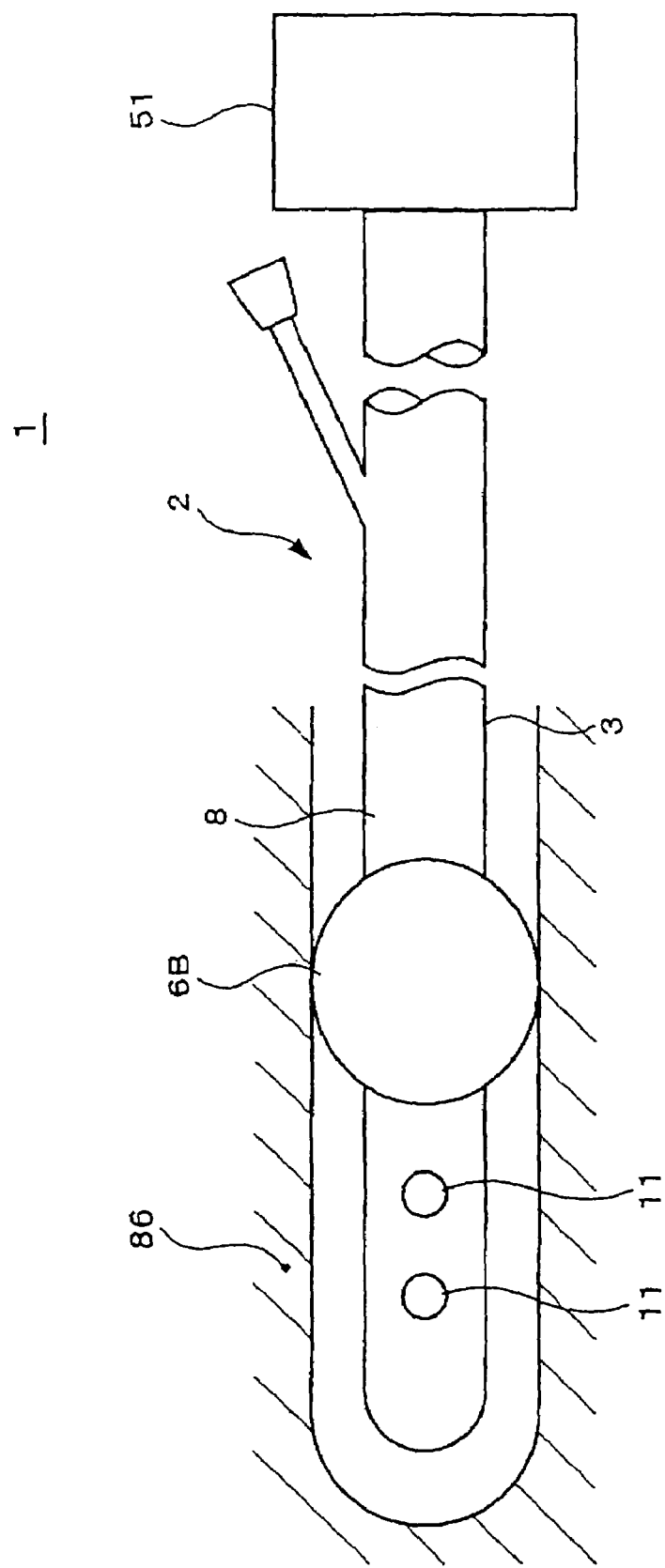
FIG. 14 is a perspective view of another example of a retaining device incorporated in the medical therapeutic apparatus.

In the above-described medical therapeutic apparatus, the retaining mechanism for retaining the liquid when the liquid is delivered is formed as a liquid-tight region in a body cavity by the pair of balloons 6A, 6B or the pair of balloons 36A, 36B. However, the retaining mechanism may be formed of other structures. For example, if the retaining mechanism is applied to the medical therapeutic apparatus 1 shown in FIG. 2, then as shown in FIG. 14, of the balloons 6A, 6B on the catheter body 3, the balloon 6A on the distal end is not used or is dispensed with, and only the rear balloon 6B is used. The catheter body 3 is inserted into a living body 86 having a closed end as shown in FIG. 14, and the balloon 6B is expanded into intimate contact with a living body wall. At this time, the region which is formed from the balloon 6B toward the distal end of the catheter body 3 is in a liquid-tight state, and serving as a retaining mechanism for retaining a liquid when the liquid is delivered. The retaining means shown in FIG. 14 is also applicable to the medical therapeutic apparatus 31 shown in FIG. 9. For example, only one of the balloons 36B is used, and when it is inserted into a living body 86 having a closed end, the expanded balloon 36B provides a retaining mechanism for retaining a liquid in the region which is formed from the expanded balloon 6B toward the distal end of the catheter body.

In the above-described example, the prostate gland is stimulated and contracted to force out the bodily secretion in the prostate gland. However, the prostate gland may not be stimulated, but the liquid in the prostate gland may be discharged by being drawn by a pump or under its head as a drawing action through the lumen, or being discharged of its own accord rather than being drawn. However, care should be taken to prevent the prostate gland cavity from remaining contracted by a quick drawing action even after the drawing of the liquid is over. In this case, the process of massaging or pressing the prostate gland 14 to contract the prostate gland 14 is not necessary.

Various examples of means for delivering a liquid and means for discharging a liquid may be incorporated, as described below. Examples of means for delivering a liquid are described below.

1. A liquid is introduced by applying a positive pressure from outside of the body.

2. A liquid is introduced of its own accord under its head or a motion tending to return from a contracted state to an original state outside of the body.

Examples of means for discharging a liquid are described below.

1. A target region is contracted by a massaging or pressing action inside of the body, and a liquid is discharged by being drawn under a negative pressure applied outside of the body.

2. A target region is contracted by a massaging or pressing action inside of the body, and a liquid is discharged by not being drawn under a negative pressure applied outside of the body.

3. No massaging or pressing action is made inside of the body, but a liquid is discharged by being drawn under a negative pressure applied outside of the body, utilizing a motion of natural contraction tending to return from an expanded state to an original state.

4. No massaging or pressing action is made inside of the body, but a liquid is discharged by not being drawn under a negative pressure applied outside of the body, utilizing a motion of natural contraction tending to return from an expanded state to an original state.

Next, with reference to FIGS. 15 to 17, various modes of usage of the medical therapeutic apparatus are described by reference to the illustrated flowcharts.

Figure 15:
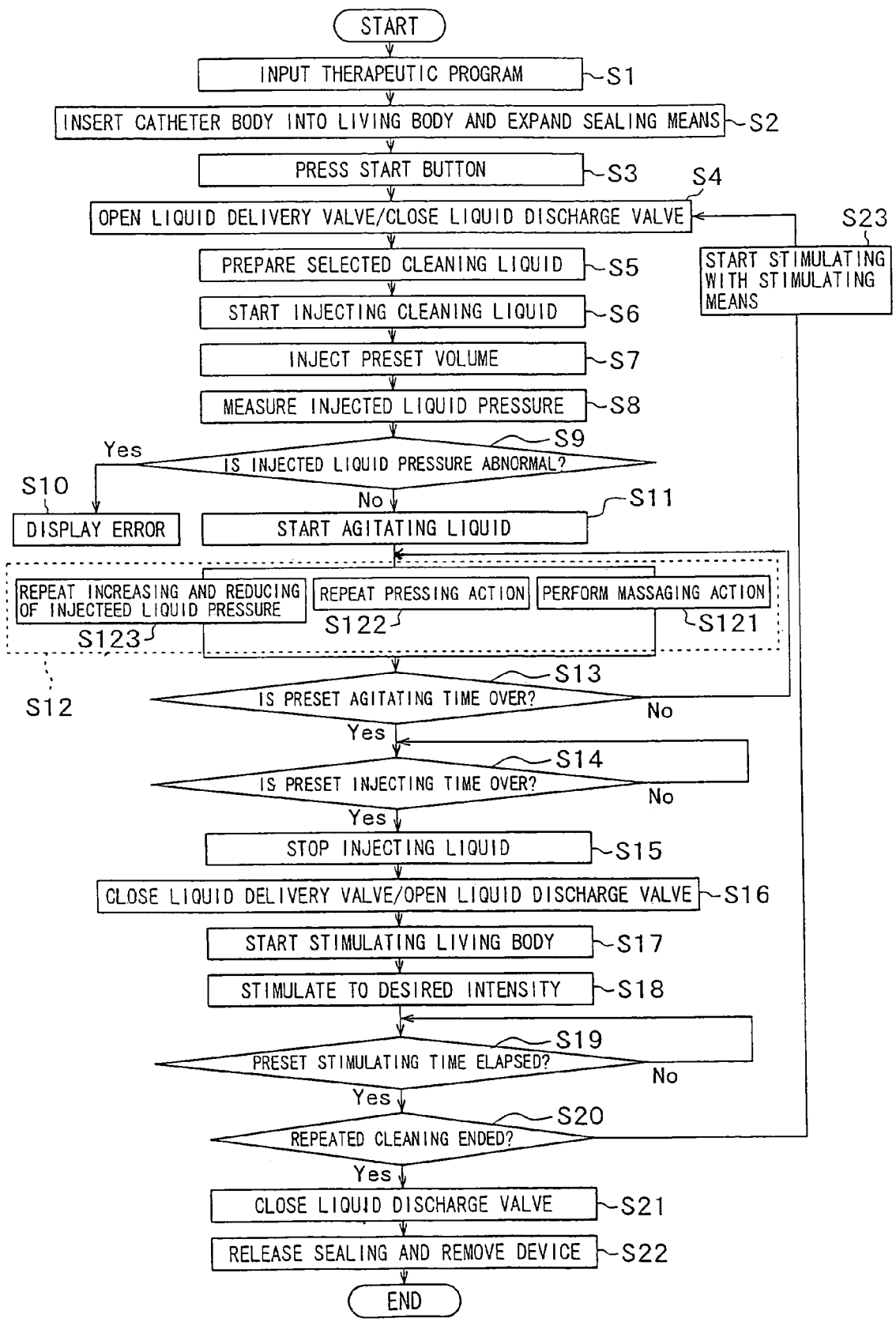
FIG. 15 is a flowchart showing a mode of usage or manner of operation of the medical therapeutic apparatus.

FIG. 15 is a flowchart showing one mode of usage of the medical therapeutic apparatus that is concerned with the synchronization of stimulation, cleaning, and agitation for delivering a liquid into a living body region in its entirety after the liquid has been introduced into the living body region.

After the sequence is started, a therapeutic program is input in step S1. For example, settings can be input relating to the number of cleaning cycles and the amount of a component contained in a discharged liquid, as well as settings of selected liquids (a cleaning liquid and a drug solution), settings of introducing times/volumes/introducing pressures of liquids, settings of stimulating time/stimulating intensity (e.g., settings of pressing time/pressing intensity, and settings of massaging time/massaging intensity). In step S2, the catheter body is inserted into the living body, and the balloons as the sealing means are expanded. The physical stimulating means is inserted into the rectum. In step S3, the start button is pressed.

In step S4, the liquid delivery valve is opened and the liquid discharge valve is closed. Thus, the liquid delivery passage is opened and the liquid discharge passage is closed. In step S5, the selected cleaning liquid is prepared. In step S6, the cleaning liquid starts to be introduced into the living body. In step S7, the cleaning liquid is introduced in the preset amount (volume).

In step S8, the pressure under which the cleaning liquid is introduced is measured. In step S9, it is determined whether the pressure is normal or abnormal. If abnormal, then an error is displayed and the apparatus is shut off (see step S10). If normal, then the control proceeds to step S11 in which the cleaning liquid starts to be agitated so that the cleaning liquid introduced into the target living body region is delivered uniformly to the living body region. In step S12, the operation of the selected agitating means is repeated. For example, a massaging action is selected and performed (see step S121). Alternatively, pressing means is selected and its pressing action is repeated (see step S122). Further alternatively, a pressure under which the cleaning liquid is introduced is selected and a cycle of increasing and reducing the pressure is repeated (see step S123). It is then determined in step S13 whether the preset agitating time is over or not. If it is not over, the control returns to step S12. If it is over, then the control goes to step S14.

In step S14, the elapse of the preset time for introducing the cleaning liquid is determined. If the preset time is not reached, then the control returns to step S14. If the preset time is reached, the control goes to step S15 in which the cleaning liquid stops being introduced. In step S16, the liquid delivery valve is closed and the liquid discharge valve is opened. Thus, the liquid delivery passage is closed and the liquid discharge passage is opened.

In step S17, the target living body region start being stimulated. For example, the pressing means starts pressing the living body region or the massaging means starts massaging the living body region. In step S18, the living body region is stimulated to a desired intensity. For example, if the living body region is to be pressed, it is pressed to a desired pressure, and if the living body region is to be massaged, it is massaged to a desired intensity. In step S19, it is determined whether the preset stimulating time has elapsed or not. If the preset stimulating time is not reached, then control returns to step S19. If the preset stimulating time is reached, then control goes to step S20.

In step S20, it is determined whether the number of cleaning cycles has reached a predetermined number or the cleaning degree of the cleaning liquid is determined. The cleaning degree can be determined based on a component contained in the discharged liquid. For example, the amount of the component is measured to determine whether or not it is equal to or less than a predetermined level. The amount of the component can be known from the level of white turbidity of the discharged liquid. For example, the amount of the component may be determined by (1) the observation with a naked eye, (2) the measurement of the transmissivity of light with a sensor, (3) the measurement of the electric conductivity with a sensor, (4) the counting of bacteria, or (5) the measurement of pH.

If the number of cleaning cycles has not reached the predetermined number or the cleaning degree of the cleaning liquid has not reached a predetermined level in step S20, then control goes to step S23 in which the stimulating means starts stimulating the prostate gland. Then, control goes back to step S4 to repeat the cleaning process. If the number of cleaning cycles has reached the predetermined number or the cleaning degree of the cleaning liquid has reached the predetermined level, the liquid discharge valve is closed in step S21. In step S22, the balloons as the sealing devices are contracted, thus canceling the sealing, and the catheter body and the stimulating means in the rectum are removed.

If the therapeutic process is directed to only the cleaning of the target living body region, then the therapeutic process is finished. If a drug solution is to be introduced into the target region after it has been cleaned, then a selected drug solution is introduced into the living body region after step S21 in which the liquid discharge valve is closed. Then, in step S22, the catheter body and the stimulating mechanisms are removed, and the therapeutic process is finished.

Figure 16:
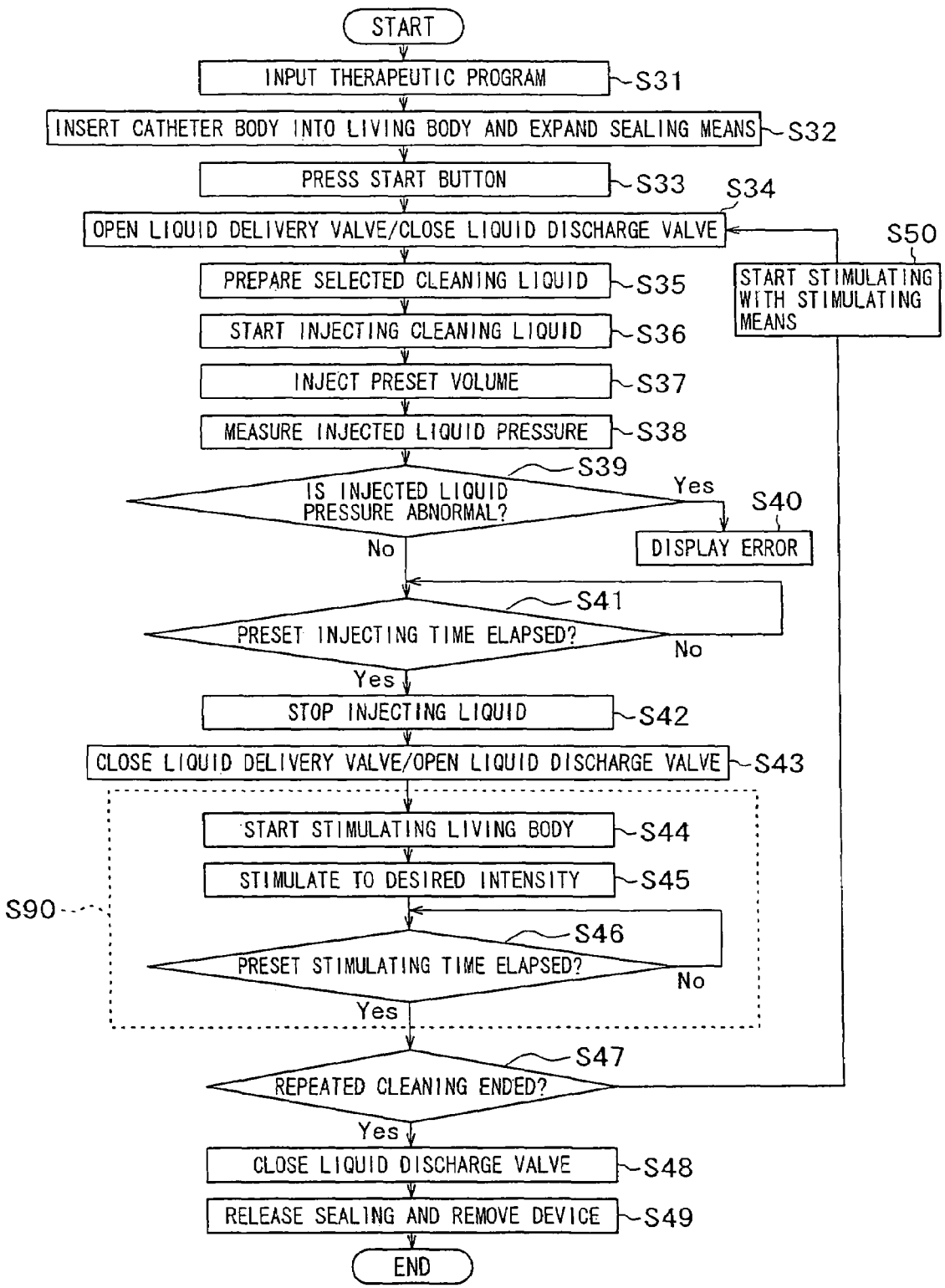
FIG. 16 is a flowchart showing a mode of usage or manner of operation of the medical therapeutic apparatus.

FIG. 16 is a flowchart showing another mode of usage of the medical therapeutic apparatus. This manner of usage is concerned with the synchronization of stimulation and cleaning. In the present embodiment, after the sequence is started, a therapeutic program is input in step S31. By way of example, the input can include settings regarding the number of cleaning cycles and the amount of a component contained in a discharged liquid, settings of selected liquids (a cleaning liquid and a drug solution), settings of introducing times/ volumes/introducing pressures of liquids, settings of stimulating time/stimulating intensity (e.g., settings of pressing time/pressing intensity, and settings of massaging time/massaging intensity). In step S32, the catheter body is inserted into the living body, and the balloons as the sealing devices are expanded. In step S33, the start button is pressed.

In step S34, the liquid delivery valve is opened and the liquid discharge valve is closed. Thus, the liquid delivery passage is opened and the liquid discharge passage is closed. In step S35, the selected cleaning liquid is prepared. In step S36, the cleaning liquid starts to be introduced into the living body. In step S37, the cleaning liquid is introduced in the preset amount (volume).

In step S38, the pressure under which the cleaning liquid is introduced is measured. In step S39, it is determined whether the pressure is normal or abnormal. If abnormal, an error is displayed and the apparatus is shut off (see step S40). If normal, then the program goes to step S41

In step S41, the elapse of the preset time for introducing the cleaning liquid is determined. If the preset time is not reached, then control returns to step S41. If the preset time is reached, the control goes to step S42 in which the cleaning liquid stops being introduced. In step S43, the liquid delivery valve is closed and the liquid discharge valve is opened. Thus, the liquid delivery passage is closed and the liquid discharge passage is opened.

In step S44, the stimulation of the target living body region is started. For example, the pressing mechanism starts pressing the living body region or the massaging means starts massaging the living body region. In step S45, the living body region is stimulated to a desired intensity. For example, if the living body region is to be pressed, it is pressed to a desired pressure, and if the living body region is to be massaged, it is massaged to a desired intensity. In step S46, it is determined whether or not the preset stimulating time has elapsed. If the preset stimulating time is not reached, the control returns to step S46. If the preset stimulating time is reached, then control goes to step S47. If the liquid in the living body region is to be discharged of its own accord, then the processing in steps S42 through S46 enclosed by the broken line is dispensed.

In step S47, it is determined whether the number of cleaning cycles has reached a predetermined number or the cleaning degree of the cleaning liquid is determined. The cleaning degree can be determined based on a component contained in the discharged liquid. For example, the amount of the component is measured to determine whether or not it is equal to or less than a predetermined level. The amount of the component can be known from the level of white turbidity of the discharged liquid. For example, the amount of the component may be determined by either (1) observation with a naked eye, (2) measurement of the transmissivity of light with a sensor, (3) measurement of the electric conductivity with a sensor, (4) counting bacteria, or (5) measurement of pH.

If the number of cleaning cycles has not reached the predetermined number or the cleaning degree of the cleaning liquid has not reached a predetermined level in step S47, the control goes to step S50 in which the stimulating means starts stimulating the prostate gland. Then, control goes back to step S34 to repeat the cleaning process. If the number of cleaning cycles has reached the predetermined number or the cleaning degree of the cleaning liquid has reached the predetermined level, the control goes to step S48 in which the liquid discharge valve is closed. In step S49, the balloons serving as the sealing mechanisms are contracted, thus canceling the sealing, and the catheter body and the stimulating mechanisms in the rectum are removed.

If the therapeutic process is directed to only the cleaning of the target living body region, the therapeutic process is finished. On the other hand, if a drug solution is to be introduced into the target region after it has been cleaned, a selected drug solution is introduced into the living body region after step S48 in which the liquid discharge valve is closed. Then, in step S49, the catheter body and the stimulating means are removed, and the therapeutic process is finished.

Figure 17:
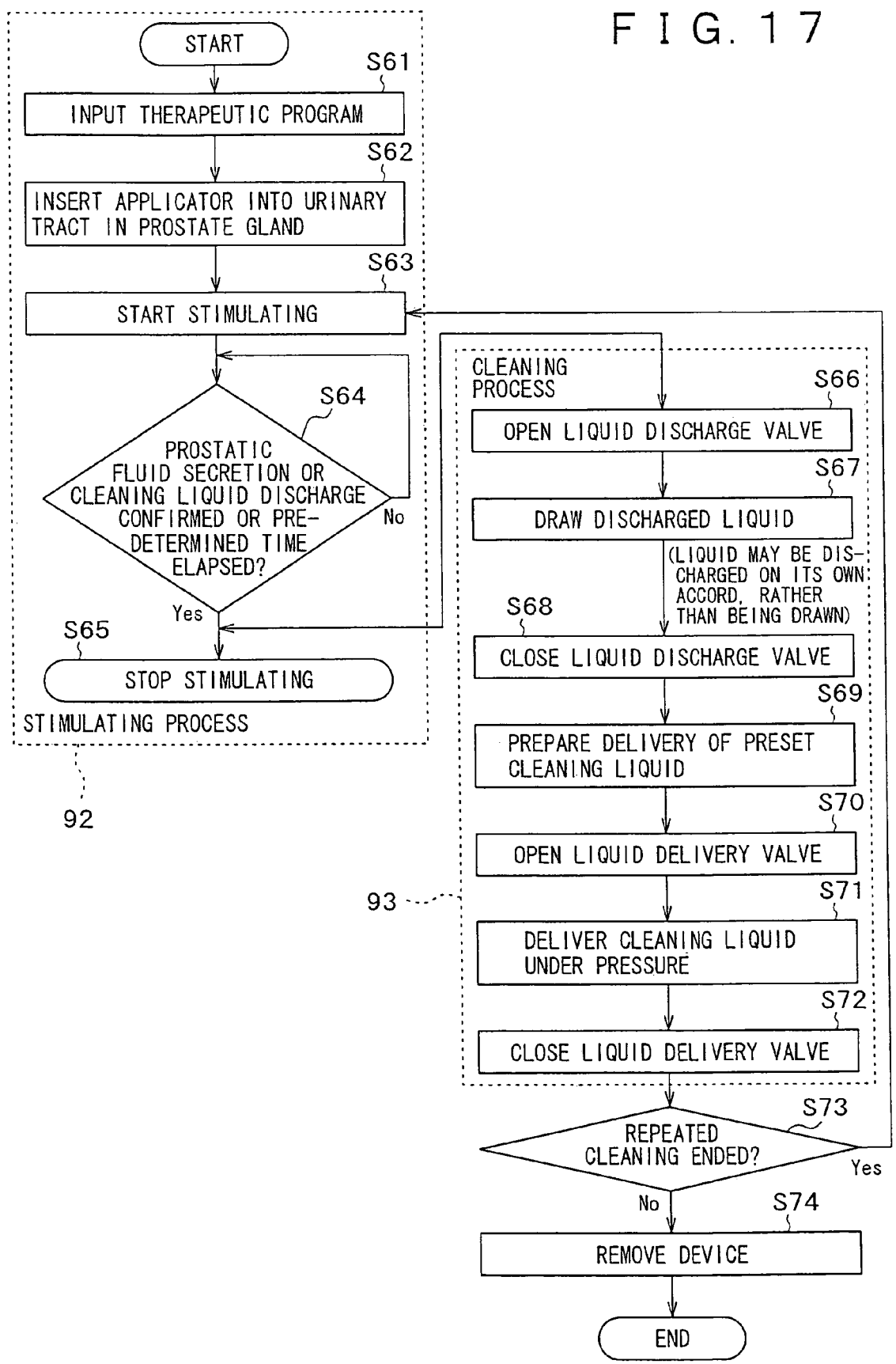
FIG. 17 is a flowchart showing a mode of usage or manner of operation of the medical therapeutic apparatus.

FIG. 17 is a flowchart showing a mode of usage of the medical therapeutic apparatus according to another embodiment. The flowchart in this embodiment is concerned with the synchronization of stimulation and cleaning for an application applied to a prostate gland cleaning apparatus.

In this embodiment, after the sequence is started, a therapeutic program is input in step S61. For example, the input here can include settings of the number of cleaning cycles and the amount of a component contained in a discharged liquid, settings of selected liquids (a cleaning liquid and a drug solution), settings of stimulating time, liquid discharge/ delivery timings, and pressures. In step S62, the catheter body is inserted into the prostatic urinary tract. Also, the physical stimulating mechanism is inserted into the rectum.

Now, the control enters a stimulating process 92. Specifically, in step S63, the prostate gland starts being stimulated. For example, the prostate gland starts being pressed or massaged. In step S64, a secretion of the prostatic fluid (i.e., for repetitive cleaning, a discharge of the cleaning liquid from the prostate gland, so-called oozing) is confirmed. It is also determined whether a predetermined time has elapsed from the start of the stimulation. If a secretion of the prostatic fluid is not confirmed, then control goes back to step S64. If a secretion of the prostatic fluid is confirmed, the control goes to step S66 of a cleaning process 93. If an oozing of the cleaning liquid from the prostate gland is not confirmed, the control returns to step S64. If the cleaning liquid is confirmed, the control goes to step S66 of the cleaning process 93. If the predetermined time has not elapsed, the control returns to step S64. If the predetermined time has elapsed, the control goes to step S66 of the cleaning process 93. In this case, control goes to step S66 while the prostatic gland is being continuously stimulated.

step S66, the liquid discharge valve is opened to open the liquid discharge passage. In step S67, the discharged liquid (the prostatic fluid or the cleaning liquid) is drawn out of the living body. At this time, the liquid may be discharged of its own accord, rather than being drawn. In step S68, the liquid discharge valve is closed.

In the stimulating process 92, if a secretion of the prostatic fluid (or the cleaning liquid from the prostate gland) is confirmed or the predetermined time has elapsed, the prostate gland stops being stimulated in step S65. After prostate gland stops being stimulated in step S65 in the stimulating process 92, the liquid discharge valve is closed in step S68.

The cleaning process 93 will be described again below. After step S68, the preset cleaning liquid is prepared for being delivered in step S69. In step S70, the liquid delivery valve is opened to open the liquid delivery passage. In step S71, a pressure is applied to deliver the cleaning liquid. After the cleaning liquid is delivered, the liquid delivery valve is closed in step S72.

In step S73, it is determined whether the number of cleaning cycles has reached a predetermined number or the cleaning degree of the cleaning liquid is determined. The cleaning degree can be determined based on a component contained in the discharged liquid. For example, the amount of the component is measured to determine whether or not it is equal to or less than a predetermined level. The amount of the component can be known from the level of white turbidity of the discharged liquid. For example, the amount of the component may be determined by either (1) observation with a naked eye, (2) measurement of the transmissivity of light with a sensor, (3) measurement of the electric conductivity with a sensor, (4) counting of bacteria, or (5) measurement of pH.

If the number of cleaning cycles has not reached the predetermined number or the cleaning degree of the cleaning liquid has not reached a predetermined level in step S73, the control goes back to step S63 in which the prostate gland starts being stimulated through the rectum, and the cleaning process is repeated.

If the number of cleaning cycles has reached the predetermined number or the cleaning degree of the cleaning liquid has reached the predetermined level, the catheter body is removed in step S74. If the therapeutic process is directed to only the cleaning of the prostate gland, the therapeutic process is finished. If a drug solution is to be introduced into the prostate gland after it has been cleaned, a preset drug solution is prepared for delivery in step S69. After steps S70 through S72, the catheter body and the stimulating means are removed in step S74, and the therapeutic process is finished.

The medical therapeutic apparatus is preferably applied to the treatment of prostatitis. However, the medical therapeutic apparatus is also applicable to the treatment of living body regions including lungs, digestive systems such as stomach and intestines, kidneys, uterus, vagina, blood vessels, etc.

In the above-described embodiments, the catheter body of the medical therapeutic apparatus is inserted into a living body cavity. However, depending on the region to be treated, the living body may be incised, and the catheter body may be inserted into the incision for cleaning and dosing the region.

The medical therapeutic apparatus has the liquid discharging means for discharging a liquid in a living body out of the living body, the liquid delivering means for introducing a liquid into the living body, the retaining mechanism for retaining the liquid in a target position, and the control means for controlling the delivery and discharge of the liquid. Therefore, the medical therapeutic apparatus can clean and directly dose a target region of the living body for efficiently treating the target region.

When a passage is shared by the delivery and discharge of the liquid, then the catheter body may be simplified in structure. Also, if the retaining mechanism includes sealing devices, the retaining mechanism, i.e., a region where the liquid is retained, is made liquid-tight for introducing liquid reliably into the target region without leakage when the liquid is introduced under a necessary pressure into the target region of the living body. In those versions where the medical therapeutic apparatus has a pair of sealing devices, a liquid-tight retaining mechanism for retaining liquid can be formed in a cavity region which corresponds to the target region of the living body which lies between the pair of sealing devices, thus allowing the liquid to be reliably introduced into the target region of the living body. If the region extending from the sealing devices toward the distal end is made liquid-tight, when the catheter body is inserted into a living body cavity with a closed distal end and the present apparatus is used, the catheter body is simplified in structure, and the liquid can be reliably introduced into the target region of the living body.

If the medical therapeutic apparatus has physical means other than hands and fingers for contracting the living body, the efficiency of a process of stimulating the living body, such as pressing, massaging, or the like, is increased. Also, if the liquid delivering means has a function to introduce the liquid under pressure into the living body, the required liquid can be more reliably introduced into the target region. Additionally, by selecting an optional liquid from a plurality of liquids and introducing the selected liquid into the living body, the living body can be efficiently cleaned and dosed.

If the liquid discharging means has a function to draw in the liquid in the living body, the liquid can be more reliably discharged. Also, it is possible to dispense with pressing or massaging for contracting the living body.

When the liquid includes a cleaning liquid, the internal region of the living body can be efficiently cleaned. The cleaning efficiency can also be improved when the control means performs repetitive cleaning by setting up an optional sequence of the delivery and discharge of the liquid.

The internal region of the living body can be more reliably cleaned when the oozing of the liquid from the living body is confirmed, and the control means performs cleaning by controlling the delivery and discharge of the liquid. Also, when the liquid in the living body is discharged, the liquid to be introduced into the living body is selected, and the liquid is introduced under automatic control, the living body can be efficiently cleaned and dosed.

By providing the medical therapeutic apparatus with detecting means for detecting a component contained in the discharged liquid, the cleaning degree of the cleaning liquid can be determined based on the amount of the component contained in the discharged liquid. In this case, if the amount of the component becomes equal to or smaller than a predetermined amount, the cleaning process can be finished when sufficient cleaning is confirmed as having been performed.

The principles, preferred embodiments and modes of operation of the present invention have been described in the foregoing specification. However, the invention which is intended to be protected is not to be construed as limited to the particular embodiments described. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the invention be embraced thereby.

What is claimed is:

1. A medical therapeutic apparatus comprising:
   a catheter body adapted to be inserted in a living body; the catheter body being provided with at least one lumen through which liquid from the living body is discharged and through which cleaning liquid is delivered to the living body; at least one inflatable balloon provided on the catheter body to seal against a portion of the living body upon inflation after the catheter body is inserted into the living body;
   a tank connected to the at least one lumen with a first valve and adapted to contain the cleaning liquid that is to be delivered to the living body;
   a container connected to the at least one lumen with a second valve for receiving the liquid that is discharged from the living body;
   a stimulating device separate from the catheter body which stimulates against a portion of the living body to stimulate the living body; and a control means configured to selectively open and close the first and second valves for controlling the discharging of the liquid from the living body to the container and the delivery of the cleaning liquid from the tank to the living body, wherein the control means also controls the stimulating device.

2. The medical therapeutic apparatus according to claim 1, wherein the at least one lumen in the catheter body through which the liquid from the living body is discharged and through which cleaning liquid is delivered to the living body liquid is a single lumen.

3. The medical therapeutic apparatus according to claim 2, further comprising a first pipe connecting the single lumen to the tank and a second pipe connecting the single lumen to the container, wherein the first valve is disposed along the first pipe and the second valve is disposed along the second pipe.

4. The medical therapeutic apparatus according to claim 1, wherein the tank comprises a first tank, and including at least one additional tank adapted to contain a cleaning liquid different from the cleaning liquid in the first tank.

5. The medical therapeutic apparatus according to claim 1, wherein the balloon is a first balloon, and further comprising a second balloon on the catheter body.

6. The medical therapeutic apparatus according to claim 5, wherein the catheter body comprises an inner catheter member and a sheath movably positioned on the inner catheter member, the second balloon being movable together with the sheath.

7. The medical therapeutic apparatus according to claim 1, wherein the stimulating device comprises one of a balloon and a rotor.

8. The medical therapeutic apparatus according to claim 1, wherein the stimulating device is inserted into the rectum and stimulates a prostate gland.

9. The medical therapeutic apparatus according to claim 1, wherein the catheter body is provided with a plurality of through holes to permit the liquid in the living body to flow into the at least one lumen and to permit cleaning liquid in the at least one lumen to flow to the living body.

* * * * *